US011311206B2

(12) United States Patent
Mulumudi et al.

(10) Patent No.: US 11,311,206 B2
(45) Date of Patent: Apr. 26, 2022

(54) DEVICES AND METHODS FOR MEASURING ANATOMIC REGIONS

(71) Applicants: Suman K. Mulumudi, Snohomish, WA (US); Mahesh S. Mulumudi, Snohomish, WA (US)

(72) Inventors: Suman K. Mulumudi, Snohomish, WA (US); Mahesh S. Mulumudi, Snohomish, WA (US)

( * ) Notice: Subject to any disclaimer, the term of this patent is extended or adjusted under 35 U.S.C. 154(b) by 0 days.

(21) Appl. No.: 16/356,520

(22) Filed: Mar. 18, 2019

(65) Prior Publication Data

US 2020/0015704 A1 Jan. 16, 2020

Related U.S. Application Data

(63) Continuation of application No. 14/522,536, filed on Oct. 23, 2014, now Pat. No. 10,271,763.
(Continued)

(51) Int. Cl.
*A61B 5/06* (2006.01)
*A61B 5/00* (2006.01)
(Continued)

(52) U.S. Cl.
CPC ............ *A61B 5/065* (2013.01); *A61B 5/0084* (2013.01); *A61B 5/061* (2013.01); *A61B 5/1076* (2013.01);
(Continued)

(58) Field of Classification Search
None
See application file for complete search history.

(56) References Cited

U.S. PATENT DOCUMENTS 4,397,091 A   8/1983 Gustavsson et al.
4,563,176 A   1/1986 Gustavsson et al.
(Continued)

FOREIGN PATENT DOCUMENTS

CN   101657180 A   2/2010
EP     0050606 B1   7/1984
(Continued)

OTHER PUBLICATIONS

International Search Report and Written Opinion in PCT/US2014/062063 dated Feb. 4, 2015 in 10 pages.

*Primary Examiner* — Amelie R Davis
*Assistant Examiner* — Marjan Saboktakin
(74) *Attorney, Agent, or Firm* — Knobbe, Martens, Olson & Bear, LLP

(57) ABSTRACT

A guidewire insertion tool configured to measure a length of an anatomic region. The tool can include a housing, a light chamber, and a track at least partially extending through the light chamber. The track is adapted to guide a guidewire as it is advanced through the insertion tool. The tool can also include an optical sensor assembly in optical communication with the light chamber. The optical sensor assembly can include one or more light sources, an optical sensor, and a magnifier. The one or more light sources can be adapted to direct light toward a portion of the guidewire within the track, and the optical sensor can be adapted to receive reflected light from the portion of the guidewire within the tract. A processing unit can analyze data from the optical sensor assembly to determine the length of the anatomic region and output the measurement to a display.

19 Claims, 9 Drawing Sheets

Related U.S. Application Data

(60) Provisional application No. 61/895,282, filed on Oct. 24, 2013.

(51) Int. Cl.
*A61B 5/107* (2006.01)
*A61B 90/00* (2016.01)
*A61M 25/09* (2006.01)

(52) U.S. Cl.
CPC ... *A61B 2090/061* (2016.02); *A61B 2090/062* (2016.02); *A61M 25/09041* (2013.01)

(56) References Cited

U.S. PATENT DOCUMENTS

| | | | |
|---|---|---|---|
| 5,415,177 A | 5/1995 | Zadini et al. | |
| 5,709,661 A | 1/1998 | Van Egmond et al. | |
| 5,860,923 A | 1/1999 | Lenker et al. | |
| 8,022,931 B2 | 9/2011 | Soo et al. | |
| 8,527,033 B1 * | 9/2013 | Williams | A61M 5/46 600/424 |
| 10,271,763 B2 | 4/2019 | Mulumudi et al. | |
| 2004/0199073 A1 | 10/2004 | Ma | |
| 2007/0250006 A1 | 10/2007 | Court et al. | |
| 2008/0009675 A1 | 1/2008 | Kura | |
| 2009/0105538 A1 | 4/2009 | Dam et al. | |
| 2010/0056958 A1 * | 3/2010 | Ravi | A61B 5/1076 600/587 |
| 2011/0301501 A1 | 12/2011 | Tsunezumi | |
| 2012/0190987 A1 | 7/2012 | Hyoun et al. | |
| 2013/0230904 A1 * | 9/2013 | Suryo | C12M 31/06 435/257.1 |
| 2014/0107471 A1 * | 4/2014 | Haider | A61B 1/3132 600/424 |
| 2014/0275955 A1 * | 9/2014 | Crawford | A61B 5/061 600/409 |
| 2014/0336462 A1 | 11/2014 | Tojo et al. | |
| 2015/0119702 A1 | 4/2015 | Mulumudi et al. | |

FOREIGN PATENT DOCUMENTS

| | | | |
|---|---|---|---|
| EP | 0170783 B1 | 4/1989 | |
| EP | 0078809 B1 | 10/1989 | |
| EP | 1096966 B1 | 8/2007 | |
| EP | 1861157 A1 | 12/2007 | |
| EP | 2243067 B1 | 10/2010 | |
| JP | H08-238209 | 9/1996 | |
| JP | 2000-113575 | 4/2000 | |
| JP | 2003-139524 | 5/2003 | |
| JP | 2003-305076 | 10/2003 | |
| JP | 2004-341242 | 12/2004 | |
| JP | 2009-077765 | 4/2009 | |
| JP | 2011-206980 | 10/2011 | |
| WO | WO 1993/20876 | 10/1993 | |
| WO | WO 99/25419 | 5/1999 | |
| WO | WO 2007/109739 | 9/2007 | |
| WO | WO-2007109739 A1 * | 9/2007 | ............ G01B 11/02 |
| WO | WO 2013/115231 | 8/2013 | |
| WO | WO 2013/186269 | 12/2013 | |
| WO | WO-2013186269 A1 * | 12/2013 | ........... A61B 5/6853 |
| WO | WO 2015/061627 | 4/2015 | |

* cited by examiner

DEVICES AND METHODS FOR MEASURING ANATOMIC REGIONS

CROSS-REFERENCE TO RELATED APPLICATIONS

This application is a continuation of U.S. application Ser. No. 14/522,536, filed Oct. 23, 2014, which claims priority benefit under 35 U.S.C. 119(e) to U.S. Provisional Application No. 61/895,282, filed Oct. 24, 2013, which is hereby incorporated by reference in its entirety.

Any and all applications for which a foreign or domestic priority claim is identified in the Application Data Sheet as filed with the present application are hereby incorporated by reference under 37 CFR 1.57.

BACKGROUND

Field

The present disclosure relates to the use of guidewires or catheters to measure anatomic regions. In some embodiments, techniques and devices described herein may be used to accurately position surgical devices in the body.

Description of the Related Art

During diagnostic and therapeutic procedures, a guidewire or catheter can be inserted into the vasculature and advanced to the organ of interest, usually through a sheath. The site of insertion depends on the modality of use.

A guidewire is often inserted through a hemostatic valve disposed at a proximal end of a sheath and advanced to the organ of interest. The hemostatic valve is a passive mechanical device that facilitates the introduction of the guidewire by opening when the guidewire is inserted through the valve and closing when the guidewire is removed. The hemostatic valve provides a seal around the guidewire to limit the blood loss and leakage of contrast during procedures. Angioplasty balloons, stents, ablation devices, or other devices can be introduced over the guidewire and into the organ, thus allowing the device to travel to the target region and deliver the intended therapy.

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

During the diagnosis and treatment of vascular lesions, measuring the length of the lesions is essential for certain medical diagnoses and treatments (e.g., to select an appropriately sized balloon or implant to use), as well as for accurate, reproducible placement of diagnostic and therapeutic devices during medical and surgical procedures. Sometimes an area needs to be treated repeatedly during a medical procedure or a device needs to be placed at an identical position at which initial therapy was delivered. During these scenarios, a method of determining or measuring the initial and subsequent position of the device in relation to an anatomic lesion will increase the accuracy of diagnosis and therapy.

Figure 1:
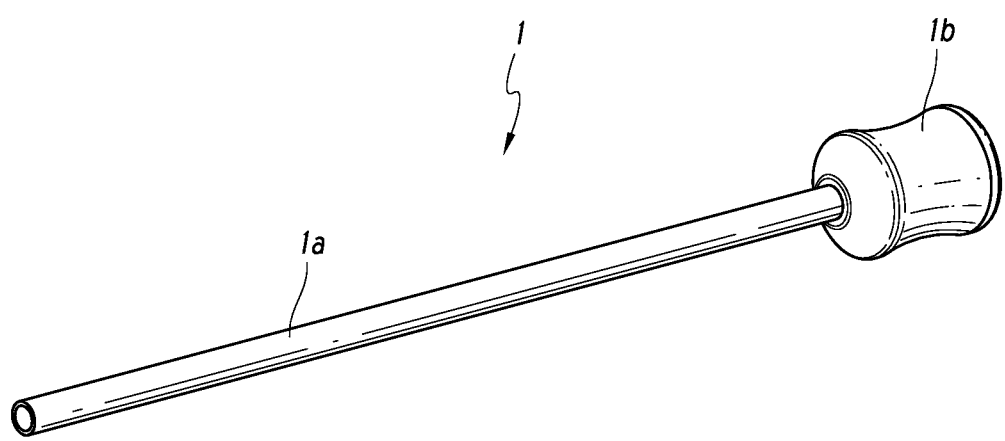
FIG. 1 is a perspective view of a wire insertion tool.

To advance a guidewire to a lesion, the guidewire can be introduced through a wire insertion tool, such as the wire insertion tool 1 illustrated in FIG. 1. The wire insertion tool 1 includes an elongate tube 1a that is connected to a hub 1b. The hub 1b is used to facilitate introduction of the guidewire into a patient's body. The elongate tube 1a is connected to the hub 1b, and includes a lumen through which the guidewire is inserted. The wire insertion tool 1 can be advanced through a guide sheath (not shown), which can include a hemostatic valve. The elongate tube 1a keeps the hemostatic valve open to prevent interference with guidewire manipulation. During the insertion of other devices (e.g., to perform an angioplasty procedure, stent implantation, ablation, or otherwise), the wire insertion tool 1 can be removed, leaving the guidewire in place. Although wire insertion tools 1 have been designed to facilitate rapid insertion and reinsertion, wire insertion tools 1 similar to those of FIG. 1 are typically passive mechanical devices with no capabilities to measure dimensions of lesions or other anatomical regions.

Anatomic lesions in arteries or veins can be visualized using angiographic images by injecting radiographic contrast (or in the case of endoscopy or laparoscopy, direct visualization). These images can be used to estimate a length of the lesion based on a size of the catheter. Alternatively, wires and catheters with fixed radiopaque or moving members with radiopaque markers can be used define the length of a lesion. However, there are challenges with measuring anatomic lesion lengths using an imaging modality such as fluoroscopy because of the tortuous nature of vascular structures. Accordingly, there is still a need for devices and methods to accurately measure the length of a lesion to facilitate accurate and reproducible placement of a surgical device at an anatomic region of interest.

Although certain devices and methods have been described herein with respect to measuring the length of a vascular lesion using a guidewire, the devices and methods described herein can be used with other diagnostic and therapeutic procedures (e.g., other transcatheter procedures, biopsies, endoscopic procedures, laparoscopic procedures, etc.) or other devices (e.g., catheters, sheaths, surgical tools, etc.).

Guidewire Insertion Tool

Figure 2:
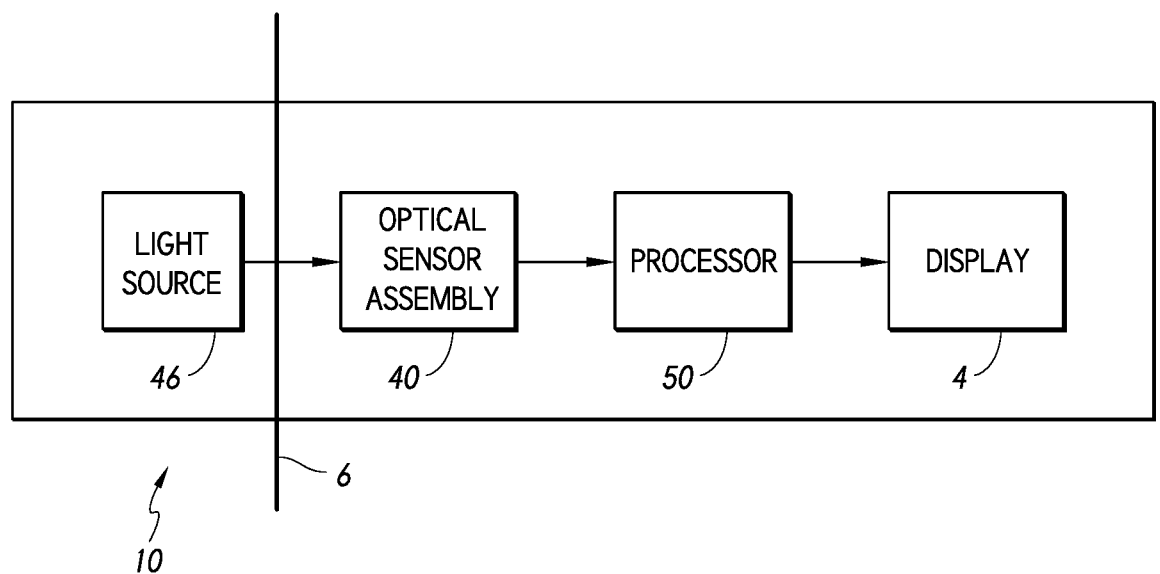
FIG. 2 is a schematic diagram of an embodiment of a guidewire insertion tool.

The present disclosure is directed toward methods and devices to measure the length of a lesion or other anatomical feature. In one embodiment, as shown in FIG. 2, such devices and methods are adapted to determine the displacement of a guidewire 6 (or catheter or other device) relative to a fixed point of a guidewire insertion tool, such as, for example, the guidewire insertion tool 10 illustrated. The guidewire insertion tool 10 is compatible with different elongate devices (e.g., guidewire, catheter, or otherwise), such that, depending on the procedure, an operator can advance the elongate device through the guidewire insertion tool 10. The guidewire insertion tool 10 can also be compatible with a guide sheath, such that the elongate device can be advanced through the guidewire insertion tool 10 and through the guiding sheath (as discussed in greater detail below with respect to FIGS. 6A and 6B, below).

Through fluoroscopic or other methods of visualization, a guidewire 6 can be advanced toward, to, and/or across a lesion. As the guidewire 6 traverses the lesion, the distance the guidewire 6 moves relative to a fixed point in the guidewire insertion tool 10, such as an optical sensor assembly 40, can be determined by the guidewire insertion tool 10. In such manner, the guidewire insertion tool 10 can include a processor 50 to determine the length of the lesion and and/or the distance from an insertion point to the beginning or end of the lesion based on the relative movement of the guidewire 6. The processor 50 can output the calculated measurement to the display 4. Using such techniques, the operator is able to accurately measure the size of a lesion to accurate select an appropriate treatment device. In some embodiments, the operator is further able to accurately and reproducibly place the surgical device in an anatomic region of interest.

Figure 3A:
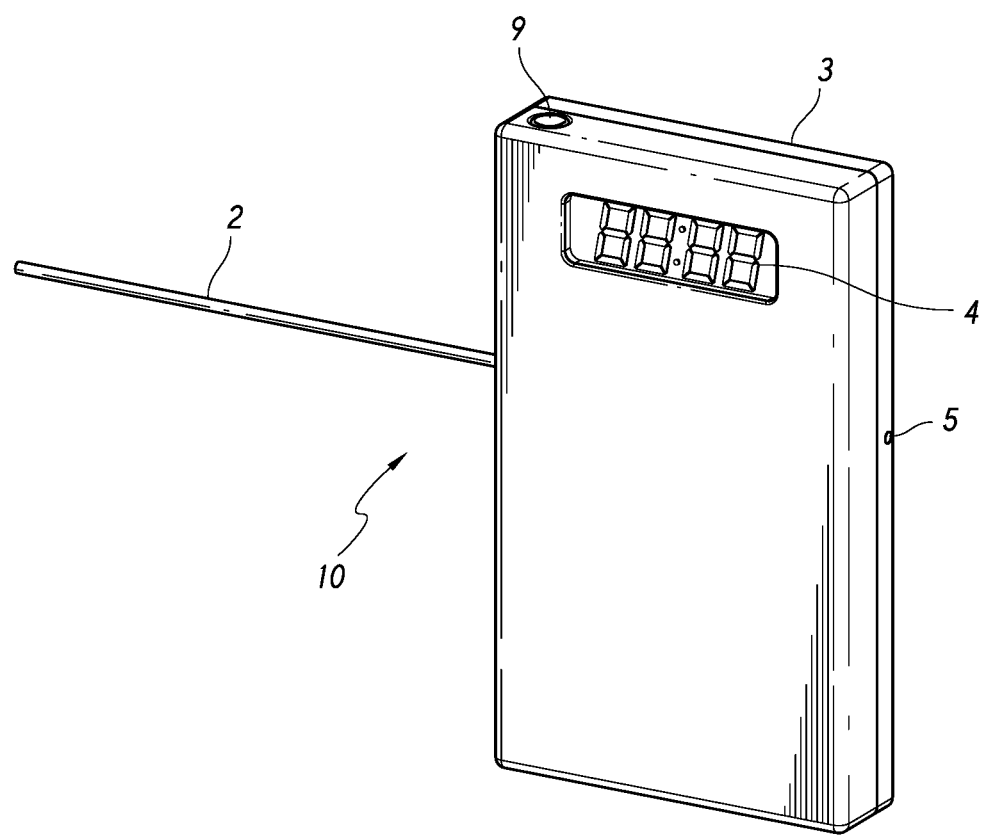
FIG. 3A is a perspective view of an embodiment of a guidewire insertion tool.
Figure 3B:
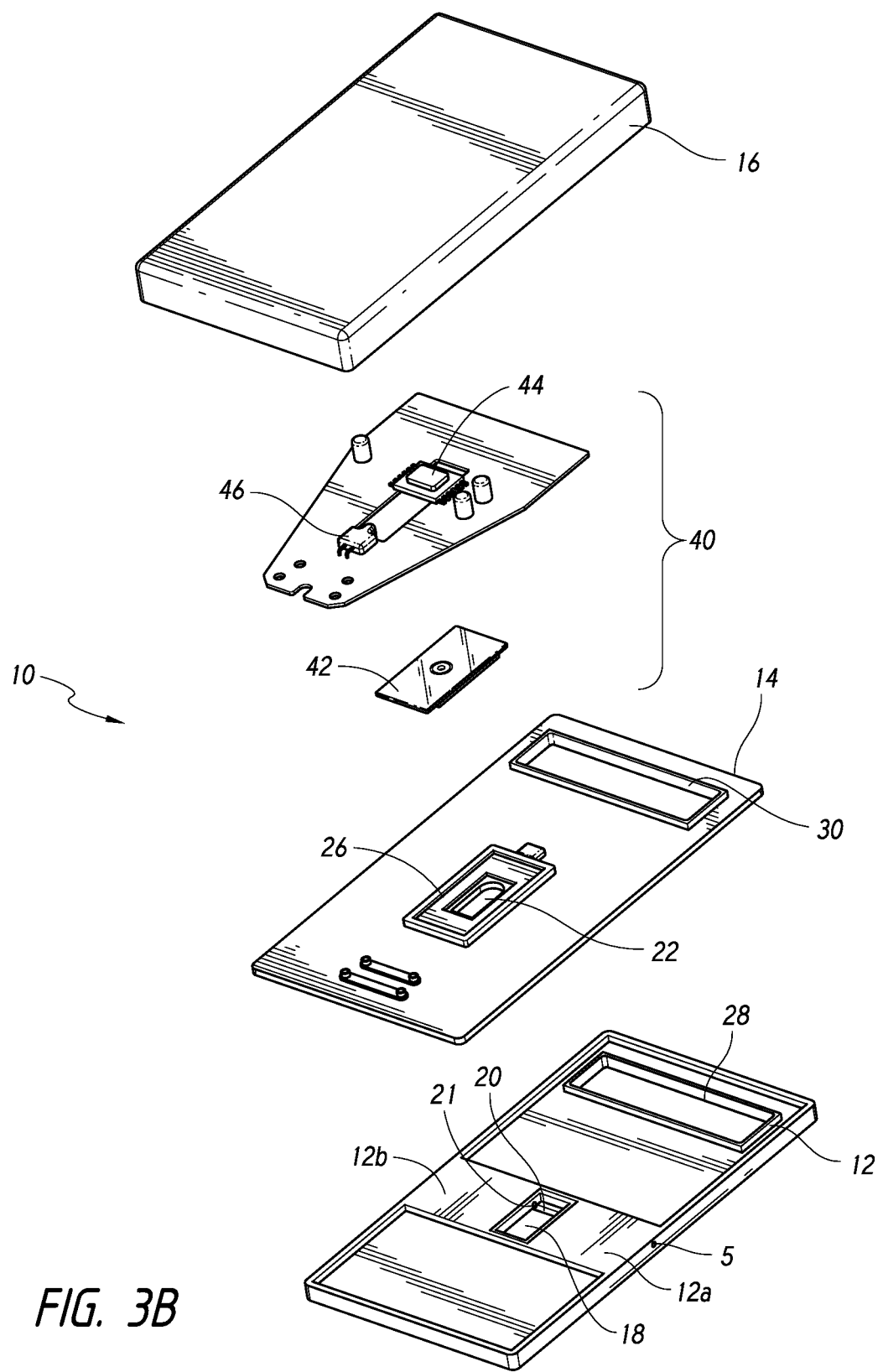
FIG. 3B is a partial exploded view of the guidewire insertion tool shown in FIG. 3A.

As illustrated in FIGS. 3A and 3B, the guidewire insertion tool 10 can include a housing 3 that accommodates and supports an optical sensor assembly 40 (see FIG. 2B). The optical sensor assembly 40 is adapted to measure the distance a guidewire (e.g., the guidewire 6 of FIGS. 6A and 6B) moves relative to a fixed point (e.g., a position of an optical sensor 44) in the guidewire insertion tool 10. During the procedure, at least the housing 3 of the guidewire insertion tool 10 (and any required power source) is positioned outside the body.

As shown in FIGS. 3A and 3B, the housing 3 can include a front portion 12, an intermediate portion 14, and a rear portion 16. The front portion 12 and the rear portion 16 can form an exterior of the guidewire insertion tool 10. The intermediate portion 14 can be positioned between the front portion 12 and the rear portion 16 and can form a lighting chamber 18 with the first portion 12. The lighting chamber 18 can span across less than about 50% of a surface of the intermediate portion, less than about 30% of a surface of the intermediate portion, less than about 15% of a surface of the intermediate portion, less than about 10% of a surface of the intermediate portion, such as between about 5% and 20% or between about 10% and about 25% of a surface of the intermediate portion.

The guidewire insertion tool 10 can include a track 20 (sometimes referred to as a tract) through which a guidewire 6 can be advanced (see FIG. 2B). The track 20 can keep the guidewire 6 in focus for detection by the optical sensor assembly 40. The track 20 can extend from an aperture 5 on the exterior of the housing 3, through the lighting chamber 18, to a needle 2 (see FIGS. 2A and 2B) positioned on the exterior surface of the housing 3. The needle 2 is adapted to interface with a guide sheath (not shown). In some embodiments, the needle 2 is omitted.

As illustrated in FIG. 2B, a majority of the track 20 is fully enclosed such that only a portion of the guidewire extending through the light chamber 18 is visible. The track 20 can include a proximal section comprising a circumferentially enclosed lumen extending through a proximal portion 12a of the front portion 12. The track 20 can include an intermediate section comprising a groove formed in the front portion 12 and extending through the light chamber. The track can include a distal section comprising a circumferentially enclosed lumen extending through a distal portion 12b of the front portion 12. The circumferentially enclosed portions of the track 20 can reduce difficulties associated with manipulating a floppy guidewire. Alternatively, the majority of the portion of the guidewire 6 extending through the track 20 can be visible. For example, the track 20 can be a groove extending across the front portion 12. The track 20 may include one or more narrow guide features to guide the guidewire through the guidewire insertion tool 10.

Figure 4A:
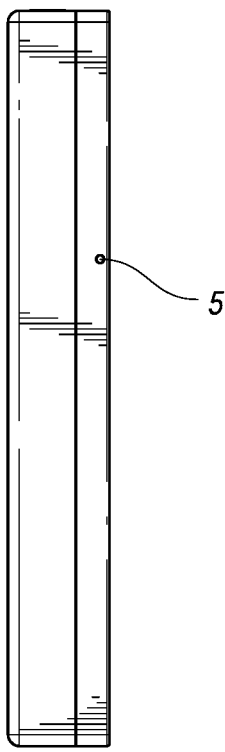
FIG. 4A is a side view of the guidewire insertion tool shown in FIG. 3A.
Figure 4B:
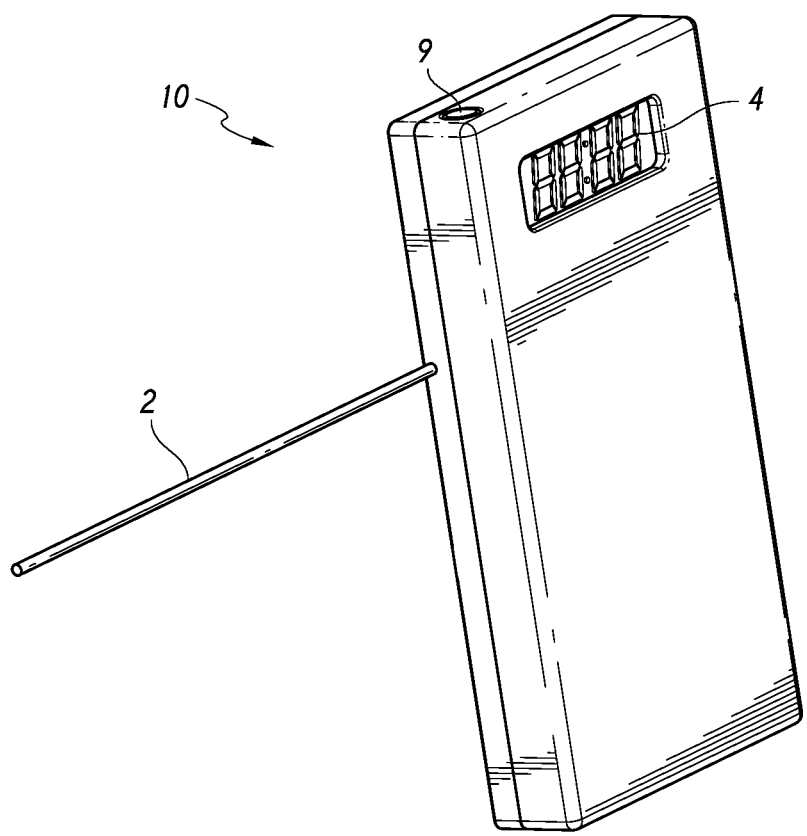
FIG. 4B is a perspective view of the guidewire insertion tool shown in FIG. 3A.
Figure 5A:
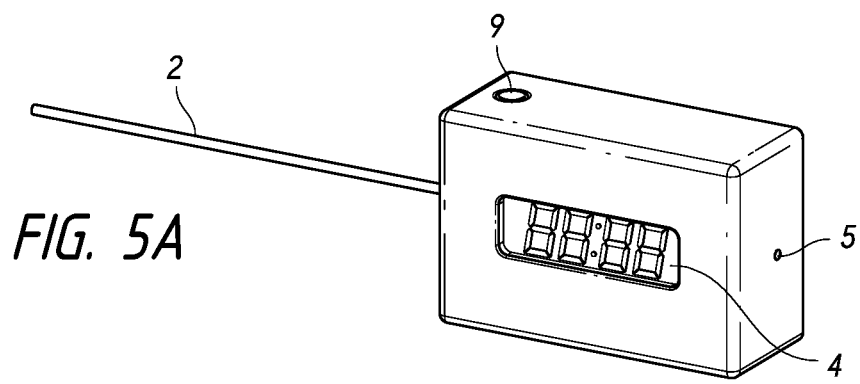
FIG. 5A is a perspective view of another embodiment of a guidewire insertion tool.
Figure 5B:
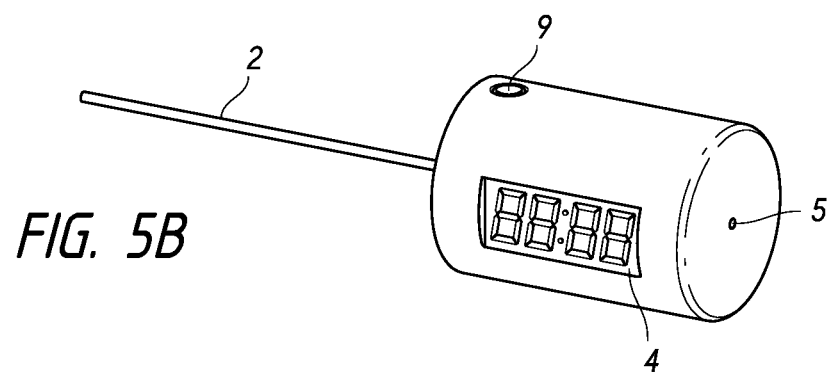
FIG. 5B is a perspective view of yet another embodiment of a guidewire insertion tool.
Figure 5C:
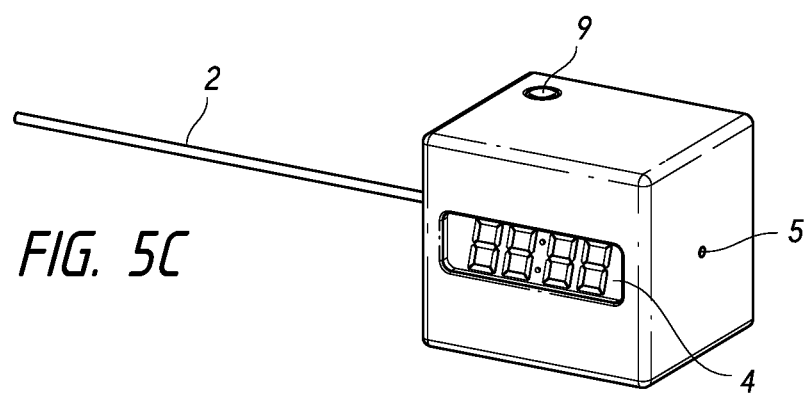
FIG. 5C is a perspective view of yet another embodiment of a guidewire insertion tool.
Figure 5D:
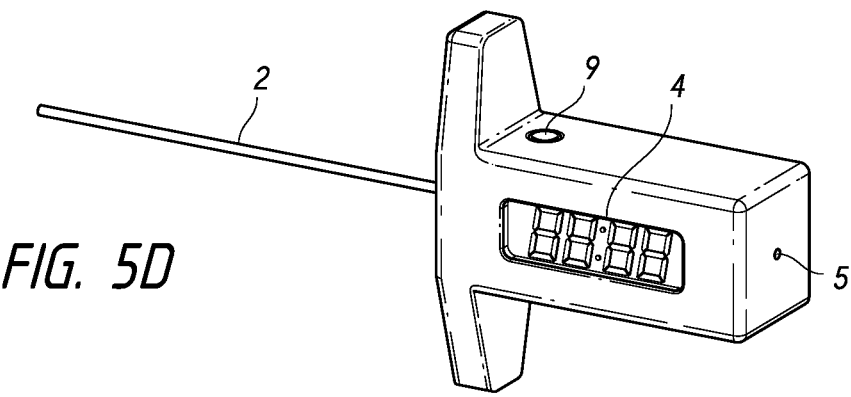
FIG. 5D is a perspective view of yet another embodiment of a guidewire insertion tool.

To facilitate manipulation of the floppy guidewire, the aperture 5 can be funnel-shaped, and can be flush with the housing 3 (see FIG. 4A) or project as appendage from the housing (not shown). Any other aperture present along the track 20, such as the aperture 21 at the distal portion 12b of the first portion 12a, can also be funnel-shaped.

The track 20 and the needle 2 can be sized to eliminate frictional interference between the hemostatic valve of the guide sheath and the guidewire 6 during guidewire manipulation. For example, the clearance between the guidewire 6 and the track 20 and/or needle 2 can be less than about 1 mm or between about 1 mm and about 10 mm, such as between about 1 mm and 5 mm. In some embodiments, the clearance is less than 1 mm. It can be desirable to reduce, minimize, or eliminate guidewire friction because such friction can interfere with the operator's tactile feel and with guidewire advancement. In some embodiments, the guidewire insertion tool 10 can include a hemostatic one-way valve to prevent the flow of body fluids and other fluids used during surgical procedures into the lighting chamber 18.

As shown in FIG. 3B, the optical sensor assembly 40 can be positioned between the intermediate portion 14 and the rear portion 16. The optical sensor assembly 40 can include a lens 42, an optical sensor 44 (e.g., a photodetector, photodiode, image sensor, optoelectronic sensor, or otherwise), and a light source 46. The optical sensor assembly 40 can be adapted to detect the movement of the guidewire 6 as it slides within the track 20. A processor (not shown) can be adapted to execute specific instructions to determine the length of the lesion based on the detected guidewire 6 movement.

If the optical sensor 44 is an image sensor, the processing unit 50 can be adapted to execute specific instructions to analyze pixel shifts between successive images (e.g., by following a surface pattern on the guidewire 6) collected by the optical sensor 44. The optical sensor 44 can capture a number of successive images per second (e.g., about 100 images/sec, about 500 images per/sec, about 1000 images per/sec, or more), each image having an array of monochromatic or chromatic pixels (e.g., 16×16, 18×18, or otherwise). As an example, the number of successive images can include a first image and a second image. The processing unit 50 can be adapted to execute specific instruction to calculate a shift in one or more pixels between the first and second images to determine the amount of guidewire movement. By analyzing pixel shifts (or changes in detected light that is emitted from the light source 46, reflected off of and/or scattered by the guidewire 6, and detected by the optical sensor 44), the processor is able to measure the distance the guidewire has traveled as the guidewire 6 moves relative to the optical sensor 44.

If the optical sensor 44 is a photodetector, the processing unit 50 can be adapted to execute specific instructions to analyze the changes in the light reflected from a surface of the guidewire 6 collected by the optical sensor 44 to measure the distance that the guidewire has traveled as the guidewire 6 moves relative to the optical sensor 44.

The particular process executed by the processor can be calibrated to measure the guidewire 6 movement in standard measurements, for example, in imperial or metric units of length and display the measurement on the electronic display 4 (see FIG. 3A). A power source (e.g., a battery, capacitor, etc.) (not shown) provides energy to one or more of the light source, processor, detector, or display.

The distance between the track 20 and the optical sensor 44 can be determined based upon the focal length of the lens 42. The focal length can be between about 1 mm and about 10 mm, for example, between about 1 mm and 5 mm, such as about 3 mm. For example, the spacing between the track 20 and the optical sensor 44 can be selected so the guidewire 6 is positioned at or near the focal length of the lens 42 when inserted into the guidewire insertion tool 10. By positioning the guidewire at the focal length (or focal point) of the lens 42, the optical sensor 44 is able to detect and measure movement of the guidewire 6 within the track 20. In some embodiments, the track 20 is a path or lumen in which a guidewire may be manipulated, e.g., advanced into the patient's body.

The intermediate portion 14 can include a window 22 that provides optical access to visualize the track 20, such that the light source 46 can illuminate the light chamber 18 and the optical sensor 44 can detect and monitor a surface of the moving guidewire 6. The presence of the light chamber 18 can concentrate the light source 46 for better visualization of the guidewire 6. The walls surrounding the light chamber 18 can be at least one of opaque, dark-colored (e.g., black), non-reflective, matte-finished, patterned, and/or textured to optimize visualization of the guidewire 6. For example, a striped wall pattern (e.g., white and black) or textured stripes can provide greater contrast between the guidewire 6 and the light chamber 18 and enhance visibility and imaging of the guidewire for image processing. The intermediate portion 14 can include a support structure 26 surrounding the window 22 to support a lens 42.

One or more light sources 46 (e.g., light emitting diode (LED), laser diode, or infrared light source) can be used as an optical source for the optical sensor assembly 40. The light sources 46 can include a direct light source or a diffuse light source. When measuring movement of a shiny elongate structure extending through the guidewire insertion tool 10, infrared light can be particularly helpful. In some embodiments, the guidewire insertion tool 10 can include a dimmer to control the intensity and/or brightness of the light emitted from the light source 46. The dimmer may be controlled by the processor and can be adjusted to select an optimal light exposure to visualize the guidewire 6.

As shown in FIG. 3B, the light source 46 and the optical sensor 44 can be positioned on opposite sides of the lighting chamber 18, e.g., the light source 46 and the optical sensor 44 can be spaced apart across a transverse plane of the guidewire insertion tool 10 or spaced apart across a longitudinal plane of the guidewire insertion tool 10. However, the optical sensor 44 and the light source 46 need not be disposed diametrically across from each other (e.g., at opposite sides of the lighting chamber 18). For example, the optical sensor 44 and the light source 46 can be offset from in multiple directions. Depending on the angle of the light emitted and the position of the optical sensor 44, the guidewire insertion tool 10 may include a prism, mirror or other technology that can directionally divert light towards the optical sensor 44.

If the guidewire insertion tool 10 includes more than one light source 46, the light sources 46 can provide light from different angles. If the light source 46 is a dual laser source, the light source 46 can cause a dark field effect to eliminate the interference from the light scatter caused by any shiny surface. If the light source 46 provides undiffused light and the guidewire 6 is shiny, the details of the guidewire 6 can be distorted as the guidewire 6 moves through the guidewire insertion tool 10. As described above, a striped wall pattern (e.g., white and black) or textured stripes can provide greater contrast between the guidewire 6 and the light chamber 18 and enhance visibility. An optical diffuser can eliminate the fixed pattern created by the light source to improve the performance of the optical sensor when tracking movement of the guidewire 6.

The lens 42 or separate transparent structure can magnify the patterns on the guidewire 6 and can be disposed between the track 20 and the optical sensor 44. Such magnification facilitates the monitoring of the guidewire 6 by enhancing minor patterns inherent on the surface of the guidewire 6.

As shown in FIG. 3A, the guidewire insertion tool 10 can include an alphanumeric display 4 that can show the distance traversed by the guidewire 6. For example, the guidewire insertion tool 10 the display 4 can be visible through openings 28, 30 in the front portion 12 and the intermediate portion 14, respectively). The guidewire insertion tool 10 can include a button 9 (or other actuator) that can zero the counter and display 4.

In some embodiments, the guidewire insertion tool 10 can include a disposable component and a reusable component. The disposable component can include one or more elements that contact the guidewire and/or operator during use. The reusable component can include light generation, detection, processing and power elements. For example, in one embodiment, the disposable component includes one or more of a housing, aperture, track, light chamber, and/or needle. The reusable component can include one or more of the processor, optical sensor assembly, and/or power source. The reusable component is adapted to attach to the disposable component and detect and measure the distance traversed by a guidewire through the track of the disposable component.

In some embodiments, the housing 3 may include more or less components than the front portion 12, intermediate portion 14, and the rear portion 16. For example, the housing 3 may not include the intermediate portion 14. Rather the optical sensor assembly 40 may include a portion of the light chamber 18, the support structure 26, and/or the window 22. As another example, the housing 3 may include additional housing components. The intermediate portion 14, the rear portion, the optical sensor assembly 40, processor 50, and/or power source can form the reusable component. The front portion 12 and an additional housing portion (not shown) can form a disposable component including the light chamber 18 and the track 20.

Although the housing 3 of the guidewire insertion tool 10 is illustrated as being a rectangular prism in FIG. 2 with the longer side extending in a transverse direction of the guidewire insertion tool 10, the housing 3 can take on other general shapes as shown in FIGS. 5A-5D, e.g., a rectangular prism with the longer side extending in a longitudinal direction of the guidewire insertion tool 10, a cylinder (see FIG. 5B), a cube (see FIG. 5C), a T-shape (FIG. 5D), a sphere, or otherwise.

Method of Use

Figure 6A:
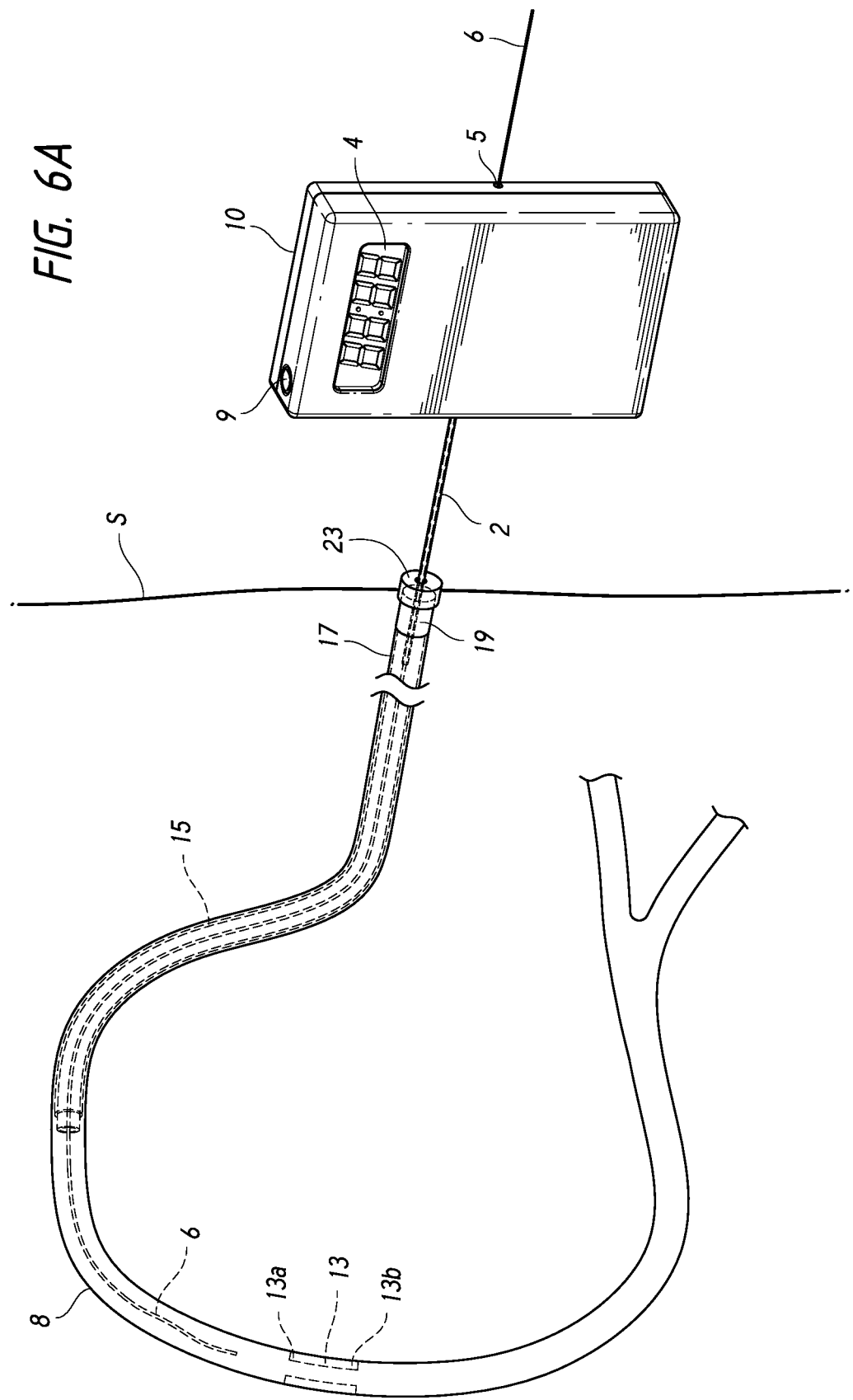
FIGS. 6A and 6B illustrate a method of using the guidewire insertion tool shown in FIG. 2A.
Figure 6B:
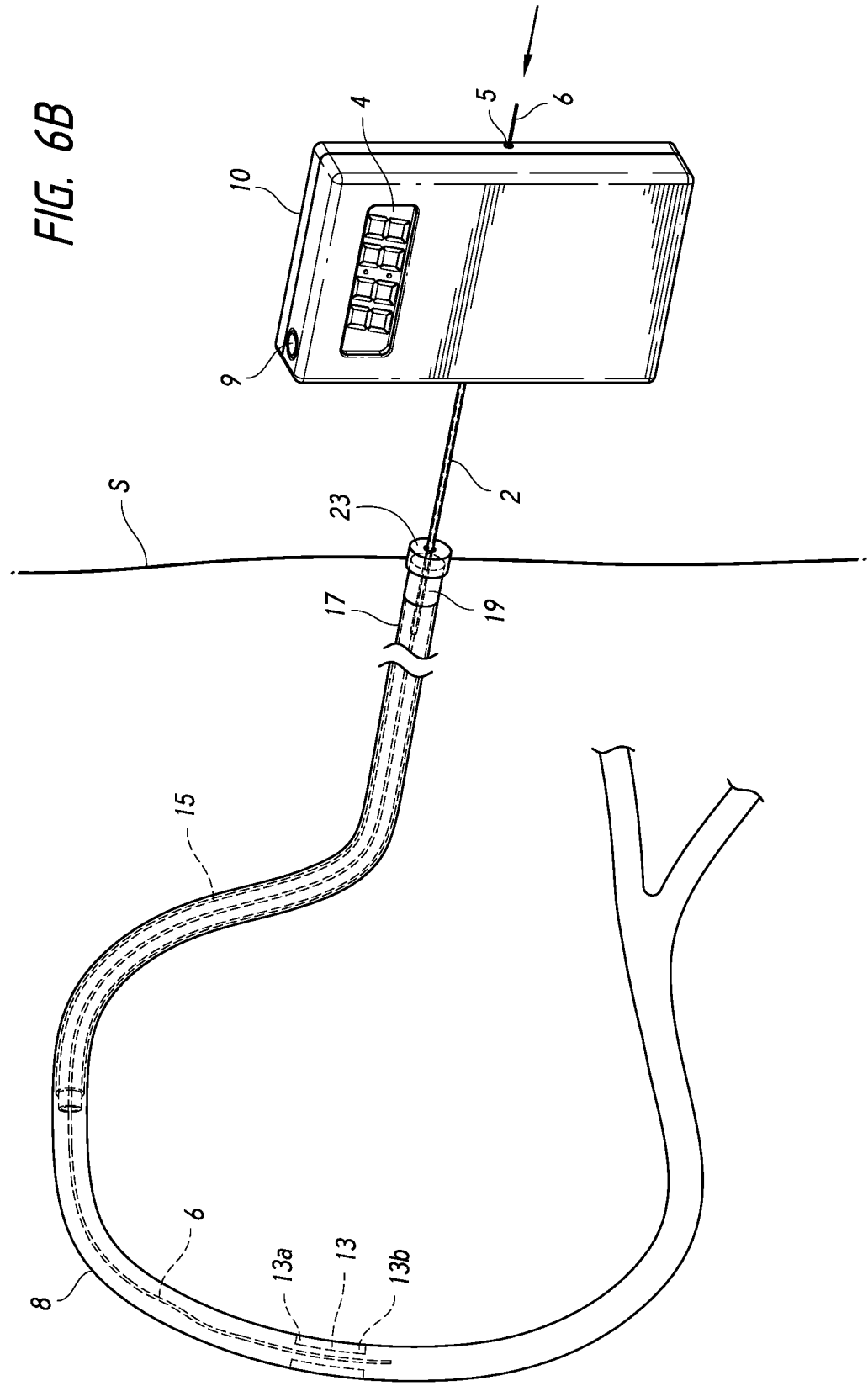

FIGS. 6A and 6B illustrate the guidewire insertion tool 10 being used during an angioplasty procedure of the right coronary artery. First, a guide sheath 17 can be positioned in the body (e.g., through a femoral artery) with a hemostatic valve enabled sheath adapter 19 resting on an outer surface of the skin S. A guiding catheter 15 can be inserted into the sheath 17 through the hemostatic valve enabled sheath adapter 19 and advanced to the coronary artery 8. The needle 2 of the guidewire insertion tool 10 can be introduced through the hemostatic valve enabled adapter 23 of the guiding catheter 15 to prevent frictional interference between the guidewire 6 and the hemostatic valve of the guide sheath 17. Such frictional interference may impede movement of the guidewire 6. The guidewire 6 is inserted into the guidewire insertion tool 10 at the aperture 5. The guidewire 6 is advanced into the guidewire insertion tool 10 such that it passes through the track 20 (not shown) and exits the guidewire insertion tool via the needle 2. Since the needle 2 is positioned within a hemostatic valve enable adapter 23 of the guiding catheter 15, the guidewire 6 is within the patient's vasculature as it exits the needle 2. The guidewire 6 is advanced to a proximal end of an angiographically visible lesion 13 (see FIG. 6A). Once the tip of the guidewire 6 is positioned at a first location 13a (e.g., positioned at the proximal end of the vascular lesion 13), the button 9 can be actuated to zero the counter and display 4. As the guidewire 6 is manually advanced and crosses the lesion 13 under fluoroscopic visualization, the distance traveled by the tip of the guidewire 6 inside the vessel 8 can be measured by the guidewire insertion tool 10 positioned outside the body. When the tip of the guidewire 6 reaches a second position 13b (e.g., the distal end of the lesion 13), the distance traversed by the guidewire 6 from the time of zeroing denotes the length of the lesion 13 (see FIG. 6B). Thereafter, the guidewire insertion tool 10 can be removed over the guidewire 6, and a catheter or other device can be advanced over the guidewire 6 and the diagnostic and/or therapeutic procedure can be performed. When the procedure is complete, the guidewire 6, the guiding catheter 15, and the guide sheath can be removed.

If a balloon or implantable device is being positioned in the vessel, the length of the lesion can help determine an appropriately sized device. For example, the user may select a balloon or implantable device (e.g., stent, etc.) having the same or greater length of the lesion. The lesion length provided by this method is more accurate than visual estimation (e.g., using fluoroscopic or other visualization techniques), which can be difficult in view of the curves and other myriad of anatomic variations in the vasculature.

The guidewire insertion tool 10 can also be used to determine a length or distance from an access point to the lesion using the method described above. After the insertion length has been determined, the tip of a different device can be advanced over the distance indicated by the electronic display 4 to enable the operator to reproducibly position the different device or reinsert the same guidewire 6 to the same location. For example, the user can reset the counter by pressing the reset button 9 as soon as the guidewire is inserted into the patient's body (e.g., at the hemostatic valve) or at another fixed location. As the guidewire is advanced to the lesion (or other anatomical target), the guidewire insertion tool 10 measures the length of guidewire passing across and through the track 20. When the guidewire reaches the anatomical target, the display 4 displays the distance from the point at which the reset button 9 was pressed to the anatomical target.

As another example, if the insertion length has been determined based on previously taken images (e.g., CT scan, x-rays, etc.), the guidewire insertion tool 10 can be used to determine whether the guidewire 6 has been advanced the pre-determined length.

Figure 7:
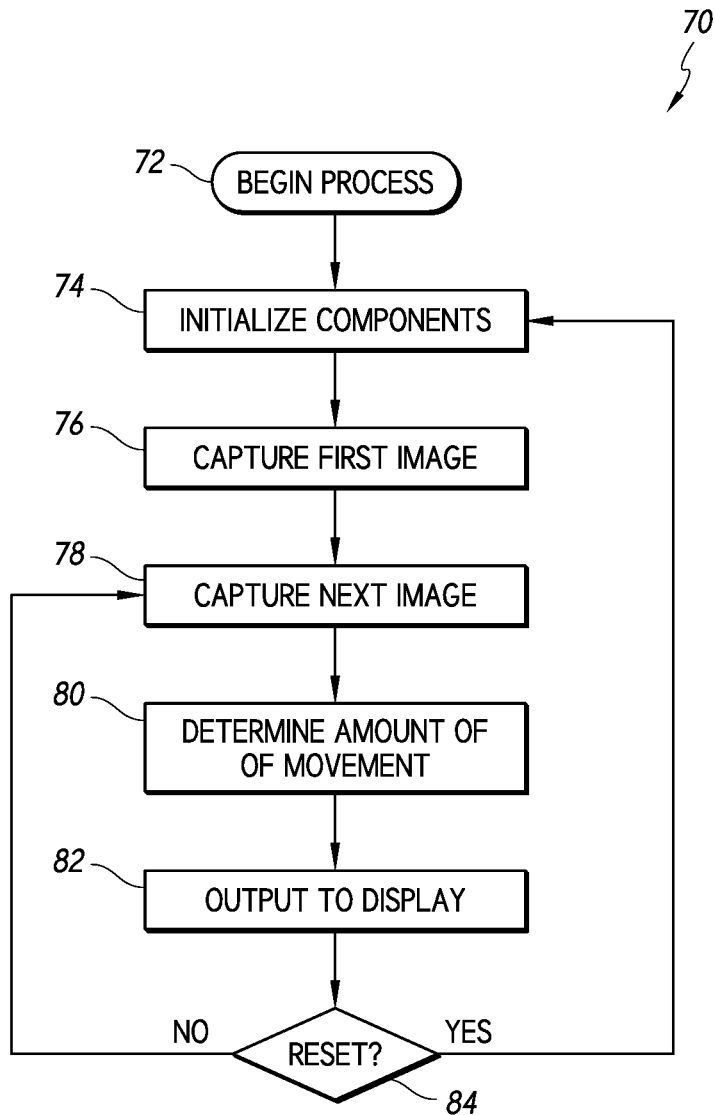
FIG. 7 is a flow chart illustrating an embodiment of method that can be used with a guidewire insertion tool.

As mentioned above, the processing unit 50 can be configured with specific instructions to analyze data collected by the optical sensor assembly 40 to convert changes in successive data collections to a length measurement. One embodiment of such process 70 is illustrated in the flow chart of FIG. 7. The process 70 begins when the operator zeros the counter, for example, by actuating the button 9 (block 72). When the process 70 begins, the light source 46 and the optical sensor assembly 46 can be activated and the counter and display can be reset (block 74). As the guidewire 6 is advanced through the guidewire insertion tool 10, the optical sensor assembly 40 can collect a plurality of data collections, e.g., a first image (block 76) and a next image (block 78). The processing unit 50 can determine the amount and direction of guidewire movement by analyzing the changes between the first and next images, e.g., by analyzing pixel shifts or changes in reflected light, to calculate a length traversed by the guidewire 6 (block 80). If the processing unit 50 determines the guidewire has been advanced, the counter can be increased. If the processing unit 50 determines the guidewire has been retracted, the counter can be decreased. The amount of movement can be output to the display 4 as a unit of length (block 82). If the process is reset (e.g., by actuation of the button 9) (block 84), the counter and display can be reinitialized (block 74). If the process is not reset, the optical sensor assembly 40 can collect the next image (block 78). This process can be continuous until the insertion tool is turned off.

Terminology

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently.

The various illustrative logical blocks, modules, routines, and algorithm steps described in connection with the embodiments disclosed herein can be implemented as electronic hardware, computer software, or combinations of both. To illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device configured with specific instructions, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing processes described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "approximately," "about," and "substantially" as used herein represent an amount close to the stated amount that still performs a desired function or achieves a desired result. For example, the terms "approximately," "about," and "substantially" may refer to an amount that is within less than 10% of the stated amount, as the context may dictate.

The term "generally" as used herein represents a value, amount, or characteristic that predominantly includes or tends toward a particular value, amount, or characteristic. As an example, in certain embodiments, as the context may dictate, the term "generally rectangular" can refer to a shape that departs from the 90 degree angles of the rectangle by less than or equal to 20 degrees. As another example, in certain embodiments, as the context may indicate, the term "generally perpendicular" can refer to an angle that departs from exactly perpendicular by less than or equal to 20 degrees.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Although certain embodiments and examples have been described herein, it will be understood by those skilled in the art that many aspects of the guidewire insertion tool shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "advancing a guidewire to a lesion" include "instructing advancement of a guidewire to a lesion."

The following is claimed:

1. An insertion tool configured to measure a length of an anatomic region, the tool comprising:
   a housing comprising an inlet and an outlet;
   a track extending through the housing from the inlet to the outlet and adapted to guide an elongate member as it is advanced through the insertion tool, the track comprising a groove; and
   an optical sensor assembly comprising:
      one or more light sources adapted to direct source light on a portion of the elongate member within the track;
      an optical sensor adapted to receive reflected light from the portion of the elongate member within the track; and
      a processing unit configured to analyze data from the optical sensor to determine the length of the anatomic region;
   wherein the groove is configured to position the elongate member within a focal length of the optical sensor assembly as the elongate member passes over the groove; wherein the groove is open toward the optical sensor assembly to expose the elongate member to the optical sensor assembly.

2. The insertion tool of claim 1, further comprising a display configured to display the length of the anatomic region.

3. The insertion tool of claim 2, wherein the display is visible through the housing.

4. The insertion tool of claim 2, wherein the display is removably connected to the housing.

5. The insertion tool of claim 1, wherein the optical sensor assembly is removably connected to the housing.

6. The insertion tool of claim 1, further comprising a light chamber having walls configured to concentrate the source light directed on the portion of the elongate member within the track, the track extending between the walls.

7. The insertion tool of claim 6, wherein the light chamber comprises a dark colored wall.

8. The insertion tool of claim 6, wherein the light chamber comprises a matte-finished wall.

9. The insertion tool of claim 6, wherein the light chamber comprises a patterned wall.

10. The insertion tool of claim 6, further comprising a magnifier configured to magnify the portion of the elongate member within the track.

11. A method of measuring a length of an anatomic region, the method comprising:
    moving an elongate member through an insertion tool and across the anatomic region, the insertion tool comprising:
       a track adapted to guide the elongate member as the elongate member moves through the insertion tool, the track comprising a groove;
       an optical sensor configured to be in optical communication with a portion the elongate member within the groove when the elongate member is moved through the insertion tool, the groove configured to position the elongate member within a focal length of the optical sensor; and
       a processing unit configured to analyze data from the optical sensor;
    positioning the portion of the elongate member within the focal length of the optical sensor as the portion of the elongate member passes over the groove;
    directing light on the portion of the elongate member within the groove;
    detecting light reflected from a surface of the elongate member using the optical sensor as the elongate member moves through the insertion tool; and
    determining the length of the anatomic region by analyzing the detected light as the elongate member moves across the anatomic region.

12. The method of claim 11, further comprising displaying the length of the anatomic region on a display.

13. The method of claim 12, further comprising resetting the length displayed on the display.

14. The method of claim 11, further comprising retracting the elongate member, wherein retracting the elongate member causes the processing unit to decrease the determined length of the anatomic region.

15. The method of claim 11, further comprising magnifying the portion of the elongate member within the groove.

16. The method of claim 11, wherein the anatomic region is a lesion.

17. The method of claim 11, wherein the elongate member is a guidewire.

18. The insertion tool of claim 1, wherein the track comprises a circumferentially-enclosed proximal section, a circumferentially-enclosed distal section, and an intermediate section therebetween, the intermediate section comprising the groove.

19. The insertion tool of claim 18, further comprising a light chamber, the intermediate section of the track being exposed to the light chamber.

* * * * *